United States Patent
Rodriguez Cerda et al.

(10) Patent No.: US 10,245,224 B2
(45) Date of Patent: Apr. 2, 2019

(54) TOPICALLY APPLIED COSMETIC REDUCTIVE COMPOSITION CONTAINING KERATIN AND SULPHUR

(71) Applicant: Patricio Alfredo Rodriguez Cerda, Santiago (CL)

(72) Inventors: Patricio Alfredo Rodriguez Cerda, Santiago (CL); Juan Pablo Morales Montecinos, Santiago (CL)

(73) Assignee: Patricio Alfredo Rodriguez Cerda (CL)

( * ) Notice: Subject to any disclaimer, the term of this patent is extended or adjusted under 35 U.S.C. 154(b) by 0 days.

(21) Appl. No.: 15/549,070

(22) PCT Filed: Feb. 29, 2016

(86) PCT No.: PCT/CL2016/000008
§ 371 (c)(1),
(2) Date: Nov. 20, 2017

(87) PCT Pub. No.: WO2016/141498
PCT Pub. Date: Sep. 15, 2016

(65) Prior Publication Data
US 2018/0147130 A1 May 31, 2018

(30) Foreign Application Priority Data
Mar. 11, 2015 (CL) .................... 593-2015

(51) Int. Cl.
| A61K 8/65 | (2006.01) |
| A61Q 19/06 | (2006.01) |
| A61K 8/23 | (2006.01) |
| A61K 8/41 | (2006.01) |
| A61K 8/42 | (2006.01) |
| A61K 8/44 | (2006.01) |
| A61K 8/46 | (2006.01) |
| A61K 8/49 | (2006.01) |
| A61K 8/60 | (2006.01) |
| A61K 8/92 | (2006.01) |

(52) U.S. Cl.
CPC .................. *A61K 8/65* (2013.01); *A61K 8/23* (2013.01); *A61K 8/41* (2013.01); *A61K 8/42* (2013.01); *A61K 8/442* (2013.01); *A61K 8/463* (2013.01); *A61K 8/494* (2013.01); *A61K 8/602* (2013.01); *A61K 8/922* (2013.01); *A61Q 19/06* (2013.01); *A61K 2800/48* (2013.01)

(58) Field of Classification Search
CPC . A61K 8/65; A61K 8/463; A61K 8/23; A61Q 19/06
See application file for complete search history.

(56) References Cited

U.S. PATENT DOCUMENTS

| 4,279,996 | A | * | 7/1981 | Yoshioka ................. A61K 8/65 |
| | | | | 424/70.14 |
| 4,948,876 | A | | 8/1990 | Bore et al. |
| 6,367,550 | B1 | | 4/2002 | Chatterji et al. |
| 6,454,004 | B2 | | 9/2002 | Reddy et al. |
| 6,454,008 | B1 | | 9/2002 | Chatterji et al. |
| 6,547,871 | B2 | | 4/2003 | Chatterji et al. |
| 6,734,146 | B2 | | 5/2004 | Chatterji et al. |
| 6,793,730 | B2 | | 9/2004 | Reddy et al. |
| 2003/0157194 | A1 | | 8/2003 | Bass |
| 2004/0210039 | A1 | | 10/2004 | Schrooyen et al. |

FOREIGN PATENT DOCUMENTS

| GB | 481164 A | 3/1938 |
| GB | 717109 A | 10/1954 |
| GB | 1108488 A | 4/1968 |
| JP | S53135199 A | 11/1978 |
| JP | H06107997 A | 4/1994 |
| WO | 2009045556 A1 | 4/2009 |
| WO | 2010105634 A1 | 9/2010 |
| WO | 2010105636 A1 | 9/2010 |

OTHER PUBLICATIONS

Nozawa, et al., "Inhibition of Lipid Biosynthesis by p-Chlorophenoxyisobutyrate (CPIB) in Tetrahymena pyriformis", J. Biochem., 1973, 74 (6) ; 1157-1163.

* cited by examiner

*Primary Examiner* — Carlos A Azpuru
(74) *Attorney, Agent, or Firm* — St. Onge Steward Johnston & Reens, LLC

(57) ABSTRACT

The invention relates to a topically applied cosmetic reductive composition containing up to 20 wt. % of hydrolyzed keratin and sulphur. The remaining components are: water, compatibilizers, surfactants, thickeners, preservatives and/or aromatics. The cosmetic composition can be used to reduce adipose tissue in different areas of the body.

36 Claims, No Drawings

TOPICALLY APPLIED COSMETIC REDUCTIVE COMPOSITION CONTAINING KERATIN AND SULPHUR

FIELD OF THE INVENTION

The present invention is a reductive cosmetic composition for topical application for deep cleaning of the skin by entrainment, with immediate or instantaneous measurable visual effect on the body, mainly referred to the abdomen area, based on hydrolyzed keratin and Sulphur. This cosmetic composition is novel as a cosmetic products, being a composition of low risk of production.

BACKGROUND OF THE INVENTION

Cosmetic and hygiene products for human use have had a steady advance in time towards the development of formulas for the deep cleaning of the skin. The deep cleansing of the skin is considered to be related to the elimination of toxins, impurities, environmental contaminants and excessive collapse of the skin and pores.

Under natural conditions, the property of keratin is known to interact with the lipids which are part of the epidermal hydrolipidic mantle. Particularly, in cosmetics is in one side related to the hydration of the skin and on the other side with the appearance of freshness (vigor and robustness). Sulphur plays a role of cosmetic skin conditioner to promote the action of hydrolyzed keratin.

Patents relating to processes for the selective removal of adipose tissue from certain parts of the human body, or complements to known slimming processes has been already described. Thus certain parts of the body are preferably affected by the thinning treatment for aesthetic or cosmetic purposes.

There are several ways to achieve weight loss for cosmetic purposes. One method that is widely marketed involves sweating. This treatment uses i.e. steam as well as special clothes designed to make the person sweat. These methods, however, are only really effective in eliminating obesity due to fluid retention. The disadvantage arises when as a result of this treatment, it necessarily causes thirst which in turn produces the fresh consumption of liquid to compensate the liquid lost. The results of such thinning are therefore for the most part very transient.

Associated with the above, physical exercise of the subject is incorporated in very different forms and often together with other methods. Said exercise can be performed by the subject or by movements induced by manual or mechanical massage. In any case, the objective is to promote the consumption of energy by the body, favoring the metabolization of fats and carbohydrates instead of deposition of fat in tissues.

The only truly fundamental methods employed for the elimination of fat deposited in tissues are those involving diet. They are commonly reduced in carbohydrate and fat intake by maintaining a high protein diet. Such a diet may or may not be supplemented by complementary drug treatments, which allow the diet to be more pleasant. Said auxiliary treatment consists in taking certain medicines, which for example produce euphoria, stimulating activity, or appetite depressing. Also other persons consume products which will swell into the stomach to give a feeling of fullness.

The basic principles of a diet with high protein content, for purposes of thinning is that the body is fed mostly with proteins, vitamins, etc., necessary for the replacement of tissue, but deliberately reduce energy-producing foods. As a result of this, the body is forced to take its reserves of energetic foods, which are found in the fat deposited in the connective tissue.

From a purely cosmetic or aesthetic point of view, these thinning diets fail, since the body will use all of the fat reserves very often from those parts of the body where they constitute a cosmetic advantage. While deposits considered ugly from the aesthetic point of view remain intact. That is, it is very often that cosmetically undesirable fat deposits yield to diet treatment only after a considerable amount of fat has been removed from other parts of the body. In women undergoing thinning treatment, they lose fat on the face and bust, but they retain the adipose tissue of the abdomen and thighs.

The mechanism by which the body stores fat and then reuses them can be described in simplified form. Fats are carried out by the blood to the connective tissue where they are deposited. Fats deposited in the connective tissue are collected by the blood when the body needs them. It is known that for the transport of fat from connective tissue to blood, fat must first be divided into its component fatty acids and glycerin. In this way fats are transported in the bloodstream. The enzyme lipase produces the cleavage of triglycerides into fatty acids and glycerin, which is normally present in blood vessels. On the other hand it is known that the action of lipase is inhibited by insulin and that the secretion by the body of insulin is increased by the presence of carbohydrates in the diet. In other words, the intake of starch and sugar promotes insulin secretion which in turn inhibits the action of lipase. This ensures that the reserve fat deposits in the body remain untouched if the subject follows a diet rich in carbohydrates. If the diet is low in carbohydrates, the insulin secretion is reduced, leaving the lipase free to act on the triglycerides of the adipose tissue which gradually disperse as the fat is transformed into fatty acids and glycerin and pass into the bloodstream.

Taken this into account, one could easily look for a intervention in the composition of blood, in order to produce a "pro-thinning" reaction. Thus, for example, 2-(p-chlorophenyloxy) isobutyrate (CPIB) was studied in the 1960s to inhibit lipid biosynthesis (Nozawa et al., J. Biochem., 1973, 74 (6), 1157-1163) and influence the lipoprotein ratio and the level of cholesterolemia. However, many other conditions of the body are linked and affected by these factors. Then, there is no real justification for a direct intervention in the composition of blood for purely aesthetic reasons.

It is therefore necessary to find effective and healthy methods of thinning which reduce the volume of the body, eliminating fats and toxins without interrupting the normal blood balance. The present invention is a solution that effectively allows to reduce the amount of adipose tissue using a completely biodegradable unguent, which uses raw materials which is harmless to the body and which is also slightly invasive at the level of the epidermis.

SUMMARY OF THE INVENTION

The present invention relates to the combination of two principal elements, hydrolyzed keratin and Sulphur, for the production of a cosmetic composition. To the use of said cosmetic composition for the deep cleansing of the skin for the removal of toxins, impurities, environmental contaminants and part of the fatness of the skin and pores.

DETAILED DESCRIPTION OF THE INVENTION

It is well known the wide variety of products developed to address aesthetic problems such as sagging, localized adiposity, body reduction and so on. However, after the first application a visual effect is not always evident, Many slimming compositions are known, for example having a draining action, i.e. reducing water retention in the skin or superficial dermis. It will act by limiting the biochemical reaction by which the fatty acids are synthesized and esterified or linked with the Glycerol to form triglycerides or fat reserve.

The compositions used for thinning acting topically may be more or less effective due to the difficulty of the thinning agent to reach the deep layer of the skin (hypodermis) in which the adipocytes are found. Therefore, it is desirable to improve the bioavailability of certain thinning active agents, in order to increase the slimming efficiency of these compositions.

The Applicant has discovered that it is possible to achieve this by combining two main elements, each of which has been used individually in cosmetics for very different purposes but never together.

The first reaction observed when doing the massage is an aspect of anserine skin. It shows the accumulation or stimulation of a transit through the follicular ostium. Anserine skin corresponds to an aspect of the skin appearing dry and rough, similar to that of the leg of a goose. The massage favors this reaction through the pore. It causes an activation of the circulation of the zone where it is applied repeatedly by emulsifying the product. During the massage process with the cosmetic composition, the accumulation of gases and toxins in the area occurs. They are attracted by the circulation that causes the exchange and the expulsion of these substances through the skin.

Due to this treatment that causes the activation of the hair musculature at the level of the ostium or anserine skin, no evidence of erythema during the session is observed, nor any obvious irritation. No detachment of the dry epidermis in the form of lamellae or desquamation. The only notable effect is the persistence of activity at the level of the follicular ostium.

Anserine skin in forensic medicine is related to piloerection, and is an involuntary contraction of erector muscles of hair follicles and causes hair to lift on the skin, an action commonly known as goosebumps. This condition of the skin is produced by changes in temperature, nerve reactions. Especially it is considered a physiological response to cold air and extreme emotions, especially fear. This combined with Sulphur produces a marked dilation in the pore, generating a rapid route of exudation of waste and elimination of gases found in the skin.

Thus, the present invention relates principally to a novel cosmetic composition for the slimming treatment comprising hydrolyzed keratin and Sulphur. In a second scope, the invention relates to the use of said novel composition to ostensibly reduce the abdominal diameter. In a final scope, the invention relates to the method of applying the cosmetic composition.

Therefore, the invention generally relates to a cosmetic procedure for producing the body reduction with a Topical Reducing Formula applicable to any part of the body which contains an excess of adipose tissue or volume by accumulation of gases and toxins. For example from the Submammary Region to Suprapuvian Region and back Lumbar Region. It is especially useful for fat Located in the Submental or Submandibular area under the Sternocleidomastoideum muscle.

In another embodiment, a method of applying the cosmetic composition is protected in a percutaneous form through massages, maintaining a constant emulsion by adding water by dripping. For each 15 ml of the cosmetic composition 60 ml of water is required. The massage is in a circular form without strongly pressing the area. It is not due to reductive massage: the Formula works by rubbing, which must be constant and shaping of the areas to be treated.

Generally, water is understood as pure water or deionized water. However, part of the water used in the compositions of the invention optionally may be chosen from mineral water or thermal water. Mineral water or thermal water, not only refers to natural sources, but also mineral or thermal water enriched with trace elements or minerals as additional components, as well as aqueous mineral prepared from purified water, demineralized or distilled.

The invention also relates to a cosmetic product comprising a synergistic mixture of hydrolyzed keratin and Sulphur in an aqueous medium in the presence of anionic, amphoteric, nonionic surfactants, thickeners, cleaning agents and preservatives.

Keratin is a protein that makes up some of our tissues, such as hair, nails or skin. They are classified as alpha keratin and beta keratin which differ in structure and components. The first contains cysteine residues between its chains of amino acids forming Sulphur bridges, which confers resistance. The second one does not have these sulfide bridges and therefore cannot be extended. Alpha keratin is part of mammalian tissues (hair, wool, horns, nails, claws, etc.). Beta keratin is harder and is part of the claws of reptiles, turtle shells, feathers and beaks of birds, etc.

Keratin proteins are well known and come from different sources like wool or leathers. Keratin is used in a wide variety of applications, including in formulations for personal care, wound care, orthopedic materials, as nutritional supplements and in the production of polymer films.

Keratin is characterized by possessing a high amount of cysteine, a very particular amino acid responsible for the Sulphur bridges in nature. Such covalent bonds impart a high degree of crosslinking of proteins in the keratin to form disulfide bonds. They are highly ordered proteins that provide the fundamental structural property in many biological tissues.

The most commonly used keratin proteins are hydrolyzed to impart sufficient solubility and facilitate inclusion in a formulation. Keratin is inherently insoluble because of the characteristically high degree of cysteine present in the protein. For example, U.S. Pat. No. 4,948,876 describes a keratin peptide produced by enzymatic hydrolysis for use as an auxiliary in dyeing processes. In general the uses of hydrolyzed keratin are very diverse, like sponges for wounds; fertilizers or laxatives. Its application sometimes escapes cosmetics, as in the case of GB481164 that uses it to prepare therapeutically valuable gold compounds; in the production of light cement (GB1108488) as an input in the production of flame retardants (GB717109) or as a fire extinguishing agent (JPS53135199); water-based ink compositions (JPH06107997). Application has also been found as a foaming agent for dispersing oil U.S. Pat. No. 6,734, 146. In U.S. Pat. Nos. 6,367,550, 6,454,004, 6,793,730, 6,547,871 and 6,454,008, examples of the use of keratin in various petroleum and industrial applications are shown.

Inventions involving keratin and Sulphur do not exist. U.S. Application US2004210039 describes the solubilization of keratin using sodium sulfide as a reducing agent. However, combining keratin and molecular Sulphur has never been described.

Sulphur is said to support many corporal functions such as liver function and contributes to the body's natural clearance. Is capable to achieve regular blood glucose levels, supports digestive function and improves the metabolism of fats and carbohydrates. Its cosmetic uses are directly linked to the health of the skin, hair and nails: it helps to remove the toxins that accumulate in the skin, fighting bacteria and fungi.

BioSulphur is a Sulphur based product very miscible in water which also solubilizes in low molar mass alcohols and surfactants. It corresponds to micrometric Sulphur stabilized with the help of fatty acids that are able to interact more easily with the epidermis. As the fatty acids are very compatible with the skin due to their hydrophilic character, the Sulphur disperses better in the skin compared to the molecular Sulphur. This allows for better penetration into the skin. In this way the bioSulphur it is able to normalize the excessive secretion of the sebaceous glands, combating topically the problems of oily skin or seborrheic dermatitis, to name a few uses. It has a mild parasiticidal, antiseptic and keratolytic action. BioSulphur is used in the form of hydroalcoholic lotions, liquid emulsions, shampoos, masks, creams, ointments, and capillary baths.

Being the composition a cosmetic composition and therefore intended for topical application, comprising a physiologically acceptable, i.e. compatibility with the skin, the use of oils which are also compatible with the epidermis is required.

Vegetable hydrocarbon oils such as liquid triglycerides of fatty acids having 4 to 10 carbon atoms such as triglycerides of heptanoic or octanoic acids or, for example, castor oil, sunflower, maize, sesame, hazelnut, apricot, arara oil, jojoba oil, are some of the possible candidates as a vehicle for cosmetic composition.

For the stabilization of the cosmetic composition castor oil has been chosen inter alia. The hydroxyl groups in castor oil are responsible for a unique combination of physical properties. They have a relatively high density and Viscosity, a good solubility in alcohols in any proportion and rather limited in aliphatic solvents. The stability of this oil is demonstrated by the use as an absolute standard for viscosity. Due to its hydroxyl groups, this oil has polar properties, which allows it to plasticize a wide variety of natural and synthetic resins, waxes, polymers and elastomers. It also has excellent lubricating properties, as well as a remarkable ability to moisten and disperse dyes, pigments and fillers.

Preferred Embodiments of the Invention

Cone is a reductive formula, elaborated with raw materials innocuous for the human being, they fulfill all the international norms that regulate cosmetic products. It has a honey color, thick texture. Studies confirm that it is a Hypoallergenic Formula and not Toxic for the human body. The formula works at the the Follicular Ostium level, producing Anserine Skin, without presenting Eritemas, Irritation or Desquamation nor exfoliating.

The Formula is able to produce a reduction in body perimeters thanks to the attraction of gases and toxins by Osmosis.

In the examples detailed below, a percutaneous application is considered which is differentiated by the working time and modality on each zone, which considers patients standing or stretcher. The application either in one or several weekly sessions. The selected tested body areas correspond to zone 1: Armhole area, Bust, Waist, Navel and Lower Belly; Zone 2: Right and Left Arm; Zone 3: Contour Legs, Right and Left Leg.

The Recommended Protocol consists in recording the patient's sizes prior the application of the cosmetic composition and afterwards, apply a massage with the Formula for 20 minutes in the area to be treated, applying drip water to generate the necessary moisturizing to perform the massage. After 20 minutes a new size measurements is recorded to see the obtained results. It is recommended to clean the area to be treated to have it free of Creams or Lotions. In such a way the Formula will be better fixed and will penetrate the skin more easily.

The obtained results indicate that the best performance is obtained with a standing patient, with constant massage for 20 minutes over the area to be reduced.

Massages over 20 minutes over the area to be treated produces minor changes in body averages. The most effective result occurs in the first 5 minutes of work and increases slightly to 20 minutes. After this time no further decreases in the treated areas are registered.

In cases of patients with a very bulky abdomen, the massage time in the area may be increased.

This formula is applied in Percutaneous form through massages, maintaining an emulsion by adding water dropwise. A constant emulsion has to be maintained to optimize the results. On average, 15 ml of Formula is applied and approximately 60 ml of water is required to comply with the protocol.

The product for topical application, when is capable to reduce the waist circumference (in the case that it was used in this area with localized adiposity), allows to be a complement to cardiometabolic treatments, seeking to optimize this parameter and thus achieve a reduction of cardiovascular risk.

Patients with better results obtained, where those to whom they were integrally treated. In cases of patients with metabolic disorders they were advised to follow a complementary pharmacological treatment depending on the compromised cardiometabolic pathologies.

The results of the treatments show that the product has a clear benefit in aesthetic parameters of sagging, localized adiposity reduction, reduction of body measurements, reduction of cardiovascular risk.

Therefore, a topically-applied cosmetic reducing composition is desired to be protected containing not more than 15% by weight of hydrolyzed keratin and Sulphur of micrometric size, the remainder being mainly water, compatibilizers, surfactants, thickeners, preservatives and/or flavoring agents.

In said cosmetic composition the amount of hydrolyzed keratin is between 1 and 10%, while the amount of Sulphur is between 0.1 and 4%, said material preferably having a micrometric particle size.

Preferably the cosmetic composition has as a first surfactant triethanolamine dodecyl sulfate in 10 and 45% weight and as a second surfactant cocamidopropyl betaine between 10 and 45% weight. As the cleansing agent disodium cocoamphodiacetate in a range of 1 to 5% is used and as a thickener methyl glucose dioleate (PEG-120) is used in a concentration ranging from 1 to 10%, preferably 7%.

As additional components but without limiting the cosmetic composition, DMFT hydantoin (1,3-bis (hydroxymethyl)-5,5-dimethylimidazolidine-2,4-dione) as a preservative is considered, in a concentration ranging from 1 To 10%, preferably 2%, IODOPROPYNYL BUTYLCARBAMATE as a conservant is used in a concentration ranging from 0.5 to 4%, preferably 1% and as a compatibilizer castor oil is used in a concentration ranging from 0.5 to 10%, more preferably 4.9%. In order to avoid the stench of the cosmetic composition 0.1% of flavoring should be considered to be added.

The cosmetic composition may furthermore be regulated in terms of consistency by appropriate selection of each of the components selected above, so that oil-in-water, water-in-oil emulsions, a lotion, a gel, an emulsion or soap may be formed, as the examples describe.

Preferably the aqueous phase represents 20 to 70% by weight relative to the total weight of the composition, preferably 20 to 50% by weight, more preferably 30 to 50% by weight with respect to the total weight of the composition.

In another embodiment of the invention, the cosmetic composition is a body thinning composition, which reduces adipose tissue, further serving for care and/or treatment of the body, including the cellulite and/or orange peel and/or thinning the silhouette, applying the formulation to the waist, hips and/or thighs. Preferably, the composition is applied over the fatty regions of the body.

Preferred Embodiments of the Invention

Amounts are expressed in g of ingredient per 100 g of composition.

Example 1: 5% Hydrolyzed Keratin and 0.1% Sulphur

| INGREDIENTS | % m/m |
|---|---|
| WATER | 40.90 |
| TRIETHANOLAMINE DODECYL SULFATE | 20.00 |
| COCAMIDOPROPYL BETAINE | 18.00 |
| DISODIUM COCOAMPHODIACETATE | 2.00 |
| METHYL GLUCOSE DIOLEATE (PEG-120) | 6.00 |
| DMFT HYDANTOIN | 2.00 |
| IODOPROPYNYL BUTYLCARBAMATE | 1.00 |
| CASTOR OIL | 4.90 |
| HYDROLYZED KERATIN | 5.00 |
| SULPHUR | 0.10 |
| FRAGRANCE | 0.10 |
| TOTAL | 100.00 |

Example 2: 1% Hydrolyzed Keratin and 4% Sulphur

| INGREDIENTS | % m/m |
|---|---|
| WATER | 20 |
| TRIETHANOLAMINE DODECYL SULFATE | 40.90 |
| COCAMIDOPROPYL BETAINE | 18.00 |
| DISODIUM COCOAMPHODIACETATE | 2.00 |
| METHYL GLUCOSE DIOLEATE (PEG-120) | 6.00 |
| DMFT HYDANTOIN | 2.00 |
| IODOPROPYNYL BUTYLCARBAMATE | 1.00 |
| CASTOR OIL | 4.90 |
| HYDROLYZED KERATIN | 1 |
| SULPHUR | 4 |
| FRAGRANCE | 0.20 |
| TOTAL | 100.00 |

Example 3: 3% Hydrolyzed Keratin and 3% Sulphur

| INGREDIENTS | % m/m |
|---|---|
| WATER | 25 |
| TRIETHANOLAMINE DODECYL SULFATE | 20.00 |
| COCAMIDOPROPYL BETAINE | 32.80 |
| DISODIUM COCOAMPHODIACETATE | 2.00 |
| METHYL GLUCOSE DIOLEATE (PEG-120) | 6.00 |
| DMFT HYDANTOIN | 2.00 |
| IODOPROPYNYL BUTYLCARBAMATE | 1.00 |
| CASTOR OIL | 4.90 |
| HYDROLYZED KERATIN | 3 |
| SULPHUR | 3 |
| FRAGRANCE | 0.30 |
| TOTAL | 100.00 |

Example 4: 4% Hydrolyzed Keratin and 2% Sulphur

| INGREDIENTS | % m/m |
|---|---|
| WATER | 30 |
| TRIETHANOLAMINE DODECYL SULFATE | 22.90 |
| COCAMIDOPROPYL BETAINE | 25.00 |
| DISODIUM COCOAMPHODIACETATE | 2.00 |
| METHYL GLUCOSE DIOLEATE (PEG-120) | 6.00 |
| DMFT HYDANTOIN | 2.00 |
| IODOPROPYNYL BUTYLCARBAMATE | 1.00 |
| CASTOR OIL | 4.90 |
| HYDROLYZED KERATIN | 4 |
| SULPHUR | 2 |
| FRAGRANCE | 0.20 |
| TOTAL | 100.00 |

Example 5: 5% Hydrolyzed Keratin and 1% Sulphur

| INGREDIENTS | % m/m |
|---|---|
| WATER | 35 |
| TRIETHANOLAMINE DODECYL SULFATE | 24.80 |
| COCAMIDOPROPYL BETAINE | 18.00 |
| DISODIUM COCOAMPHODIACETATE | 2.00 |
| METHYL GLUCOSE DIOLEATE (PEG-120) | 6.00 |
| DMFT HYDANTOIN | 2.00 |
| IODOPROPYNYL BUTYLCARBAMATE | 1.00 |
| CASTOR OIL | 4.90 |
| HYDROLYZED KERATIN | 5 |
| SULPHUR | 1 |
| FRAGRANCE | 0.30 |
| TOTAL | 100.00 |

Example 6: 7% Hydrolyzed Keratin and 0.5% Sulphur

| INGREDIENTS | % m/m |
|---|---|
| WATER | 45 |
| TRIETHANOLAMINE DODECYL SULFATE | 13.20 |

| INGREDIENTS | % m/m |
|---|---|
| COCAMIDOPROPYL BETAINE | 18.00 |
| DISODIUM COCOAMPHODIACETATE | 2.00 |
| METHYL GLUCOSE DIOLEATE (PEG-120) | 6.00 |
| DMFT HYDANTOIN | 2.00 |
| IODOPROPYNYL BUTYLCARBAMATE | 1.00 |
| CASTOR OIL | 4.90 |
| HYDROLYZED KERATIN | 7 |
| SULPHUR | 0.5 |
| FRAGRANCE | 0.40 |
| TOTAL | 100.00 |

Example 7: 10% Hydrolyzed Keratin and 05% Sulphur

| INGREDIENTS | % m/m |
|---|---|
| WATER | 50 |
| TRIETHANOLAMINE DODECYL SULFATE | 13.00 |
| COCAMIDOPROPYL BETAINE | 11.00 |
| DISODIUM COCOAMPHODIACETATE | 2.00 |
| METHYL GLUCOSE DIOLEATE (PEG-120) | 6.00 |
| DMFT HYDANTOIN | 2.00 |
| IODOPROPYNYL BUTYLCARBAMATE | 1.00 |
| CASTOR OIL | 4.80 |
| HYDROLYZED KERATIN | 10 |
| SULPHUR | 0.1 |
| FRAGRANCE | 0.10 |
| TOTAL | 100.00 |

Example 8: 5% Hydrolyzed Keratin and 0.1% Sulphur with Plants Extracts

| INGREDIENTS | % m/m |
|---|---|
| WATER | 37.8 |
| TRIETHANOLAMINE DODECYL SULFATE | 49.0 |
| COCAMIDOPROPYL BETAINE | |
| DISODIUM COCOAMPHODIACETATE | |
| METHYL GLUCOSE DIOLEATE (PEG-120) | |
| DMFT HYDANTOIN | |
| IODOPROPYNYL BUTYLCARBAMATE | |
| HYDROLYZED KERATIN | 5.0 |
| CASTOR OIL | 4.9 |
| CUCUMBER EXTRACT (CUCUMIS SATIVUS) | 2.0 |
| EXTRACT OF MAQUI LEAVES (ARISTOTELIA CHILENSIS) | 1.0 |
| SULPHUR | 0.1 |
| CITRIC ACID | 0.1 |
| FRAGRANCE | 0.1 |
| TOTAL | 100.00 |

Example 9: 5% Hydrolyzed Keratin and 0.1% Sulphur with Plants Extracts

| INGREDIENTS | % m/m |
|---|---|
| WATER | 33.8 |
| TRIETHANOLAMINE DODECYL SULFATE | 49.0 |

| INGREDIENTS | % m/m |
|---|---|
| COCAMIDOPROPYL BETAINE | |
| DISODIUM COCOAMPHODIACETATE | |
| METHYL GLUCOSE DIOLEATE (PEG-120) | |
| DMFT HYDANTOIN | |
| IODOPROPYNYL BUTYLCARBAMATE | |
| EXTRACT OF CENTELLA ASIATICA | 5.0 |
| HYDROLYZED KERATIN | 5.0 |
| CASTOR OIL | 4.9 |
| SEAWEED EXTRACT (FUCUS VESICULOSUS) | 2.0 |
| SULPHUR | 0.1 |
| CITRIC ACID | 0.1 |
| FRAGRANCE | 0.1 |
| TOTAL | 100.00 |

Example 10: 5% Hydrolyzed Keratin and 0.1% Sulphur with Plants Extracts

| INGREDIENTS | % m/m |
|---|---|
| WATER | 66.79 |
| COCOIL GLUTAMATO DISODICO | 5.00 |
| HYDROLYZED KERATIN | 5.00 |
| CASTOR OIL | 4.90 |
| COCONUT CITRATE - DISODIC GLUCOSIDE | 3.10 |
| SODIUM LAUROYL OATS AMINO-ACIDS | 3.00 |
| ALCOHOL | 2.52 |
| GLICERINE | 2.00 |
| XANTHAN GUM | 1.30 |
| SUCROSE LAURATE | 1.14 |
| GLYCERYL CAPRYLATE | 1.00 |
| FRAGRANCE | 1.00 |
| SODIC PCA (SODIUM CARBOXILATE PIRROLIDONE) | 1.00 |
| PCA GLYCERYL OLEATE | 0.9 |
| ARGININE | 0.5 |
| HYDROLYZED WHEAT PROTEIN | 0.5 |
| LACTIC ACID | 0.2 |
| SULPHUR | 0.1 |
| SODIUM PHYTATE | 0.05 |
| TOTAL | 100.00 |

Example 11: 5% Hydrolyzed Keratin and 0.1% Sulphur. (Lotion)

| INGREDIENTS | % m/m |
|---|---|
| WATER | 59.9 |
| HYDROLYZED KERTAIN | 5.00 |
| CASTOR OIL | 4.90 |
| ALCOHOL | 30.05 |
| SULPHUR | 0.1 |
| POTASIUM CARBONATE | 0.05 |
| TOTAL | 100.00 |

Example 12: 5% Hydrolyzed Keratin and 0.1% Sulphur. (Soap)

| INGREDIENTS | % m/m |
|---|---|
| PALM OIL (ELAEIS GUINEENSIS) | 23 |
| NUCIFERA COCONUT WEED OIL | 21 |
| WATER | 18 |
| OLIVE OIL | 14 |
| GLICERINE | 8 |
| HYDROLYZED KERTIN | 5.00 |
| SULPHUR | 0.1 |
| ALCOHOL | 5 |

-continued

| INGREDIENTS | % m/m |
|---|---|
| CASTOR OIL | 4.90 |
| SODIUM HIDROXDE | 1 |
| TOTAL | 100.00 |

The following tables summarize the results of perimeter measurements (in centimeters) of 20 subjects subjected to a study using preferably the reductive formula described in Example 7. Each subject presents different pathologies thus reflecting the universality of the method.

| Example 001 | | | | | | |
|---|---|---|---|---|---|---|
| Patient Information | Sex | | Femenin | | | |
| Body shape and clinical data | | | Medium body shape, Height 1.64 mts. Flabby Abs, Abdominoplasty | | | |
| | Age | | 43 year old | | | |
| | Basic Pathology | | Depression | | | |
| | Medicines | | Pristiq | | | |
| Treatment Information | Number of sessions 6 | | Working 20 minutes each Zone, reaching 60 minutes per session | | | |
| Obtained Results Body Size | | | Before | After | Diference | % Decrease |
| | Zone 1 | Sleeveless | 93 | 90.5 | −2.5 | 2.69% |
| | | Breast | 101 | 97 | −4 | 3.96% |
| | | Waist | 80 | 70.5 | −9.5 | 11.88% |
| | | Navel | 85 | 75.5 | −9.5 | 11.18 |
| | | Lower abdomen | 95.5 | 83.5 | −12 | 12.57% |
| | Zone 2 | Right Arm | 29 | 26.5 | −2.5 | 8.62% |
| | | Left Arm | 28.5 | 26.5 | −2 | 7.02% |
| | Zone 3 | Leg Contours | 79 | 74 | −5 | 6.33% |
| | | Right Leg | 51 | 46 | −5 | 9.80% |
| | | Left Leg | 52 | 46 | −6 | 11.54% |

| Example 002 | | | | | | |
|---|---|---|---|---|---|---|
| Patient Information | Sex | | Femenin | | | |
| Body shape and clinical data | | | Height 1.67 mts. 30 Kg Overwheight. Flaccid body. | | | |
| | Age | | 44 year old | | | |
| | Basic Pathology | | None | | | |
| | Medicines | | Anticonceptives | | | |
| Treatment Information | Number of sessions 9 | | Working 20 minutes each Zone, reaching 60 minutes per session | | | |
| Obtained Results Body Size | Zones | | Before | After | Diference | % Decrease |
| | Zone 1 | Sleeveless | 93 | 86 | −7 | 7.53% |
| | | Breast | 96.5 | 91 | −5.5 | 5.70% |
| | | Waist | 82 | 75.5 | −6.5 | 7.93% |
| | | Navel | 91 | 75.5 | −5.5 | 6.04% |
| | | Lower abdomen | 99 | 85.5 | −13.5 | 13.64% |
| | Zone 2 | Right Arm | 32.5 | 30.5 | −2 | 6.15% |
| | | Left Arm | 33 | 30.5 | −2.5 | 7.58% |
| | | Leg Contours | 92.5 | 79 | −13.5 | 14.59% |
| | Zone 3 | Right Leg | 56 | 48 | −8 | 14.29% |
| | | Left Leg | 56 | 50 | −6 | 10.71% |

| Example 002 | | | | | | |
|---|---|---|---|---|---|---|
| Patient Information | Sex | | Femenin | | | |
| Contexture and clinical data | | | Heigh 1.67 mts. 30 Kg Overwheight. Flaccid body. | | | |
| | Age | | 44 years | | | |
| | Basic Pathology | | None | | | |
| | Medicines | | Anticonceptives | | | |
| Treatment Information | Number of sessions 9 | | Working 20 minutes each Zone, reaching 60 minutes per session | | | |
| Obtained Results Body Size | Zones | | Before | After | Diference | % Decrease |
| | Zone 1 | Sleeveless | 93 | 86 | −7 | 7.53% |
| | | Breast | 96.5 | 91 | −5.5 | 5.70% |

-continued

|  |  |  | Before | After | Diference | % Decrease |
|---|---|---|---|---|---|---|
|  |  | Waist | 82 | 75.5 | −6.5 | 7.93% |
|  |  | Navel | 91 | 75.5 | −5.5 | 6.04% |
|  |  | Lower abdomen | 99 | 85.5 | −13.5 | 13.64% |
|  | Zone 2 | Right Arm | 32.5 | 30.5 | −2 | 6.15% |
|  |  | Left Arm | 33 | 30.5 | −2.5 | 7.58% |
|  |  | Leg Contours | 92.5 | 79 | −13.5 | 14.59% |
|  | Zone 3 | Right Leg | 56 | 48 | −8 | 14.29% |
|  |  | Left Leg | 56 | 50 | −6 | 10.71% |

Example 003

| Patient Information | Sex | | Femenin | | | |
|---|---|---|---|---|---|---|
| Contexture and clinical data | | | Height 1.65. Overweight. Thick contexture. Sedentary | | | |
|  | Age | | 30 years | | | |
|  | Basic Pathology | | Depression | | | |
|  | Medicines | | Antidepressants | | | |
| Treatment Information | Number of sessions 7 | | Working 20 minutes each zone, reaching up to 40 minutes per session | | | |

| Obtained Results Body Size | Zones | | Before | After | Diference | % Decrease |
|---|---|---|---|---|---|---|
|  | Zone 1 | Sleeveless | 92 | 88 | −4 | 4.35% |
|  |  | Breast | 101 | 95.5 | −5.5 | 5.45% |
|  |  | Waist | 83 | 79 | −4 | 4.82% |
|  |  | Navel | 93 | 83.5 | −9.5 | 10.22% |
|  |  | Lower abdomen | 95 | 89 | −6 | 6.32% |
|  | Zone 2 | Right Arm | 30.5 | 27.5 | −3 | 9.84% |
|  |  | Left Arm | 31 | 26 | −5 | 16.13% |

Example 004

| Patient Information | Sex | | Masculin | | | |
|---|---|---|---|---|---|---|
| Contexture and clinical data | | | Height 1.75 mts, Medium Contexture, Overweigth, high abdominal fat content | | | |
|  | Age | | 29 years | | | |
|  | Basic Pathology | | Depression | | | |
|  | Medicines | | Antidepressants | | | |
| Treatment Information | Number of sessions 1 | | Working 30 minutes por Zone, reaching up to 90 minutes of treatment. | | | |

| Obtained Results Body Size | Zones | | Before | After | Diference | % Decrease |
|---|---|---|---|---|---|---|
|  | Zone 1 | Sleeveless | 106 | 101 | −5 | 4.72% |
|  |  | Breast | 102 | 101 | −1 | 0.98% |
|  |  | Waist | 92 | 88.5 | −4.5 | 4.89% |
|  |  | Navel | 103 | 96.5 | −6.5 | 6.31% |
|  |  | Lower abdomen | 105 | 101 | −4 | 3.81% |
|  | Zone 2 | Right Arm | 31 | 29.5 | −1.5 | 4.84% |
|  |  | Left Arm | 30 | 29 | −1 | 3.33% |
|  | Zone 3 | Leg Contours | 108 | 103 | −5 | 4.63% |
|  |  | Right Leg | 69 | 66.5 | −2.5 | 3.62% |
|  |  | Left Leg | 67 | 65 | −2 | 2.99% |

Example 005

| Patient Information | Sex | | Femenin | | | |
|---|---|---|---|---|---|---|
| Contexture and clinical data | | | Thick contexture, Overweight, Height 1.58 mts, Healthy. | | | |
|  | Age | | 38 years | | | |
|  | Basic Pathology | | None | | | |
|  | Medicines | | None | | | |
| Treatment Information | Number of sessions 1 | | 20 minutes working time per Zone, reaching up to 60 minutes of treatment. | | | |

| Obtained Results Body Size | Zones | | Before | After | Diference | % Decrease |
|---|---|---|---|---|---|---|
|  | Zone 1 | Sleeveless | 96 | 93 | −3 | 3.13% |
|  |  | Breast | 102 | 100 | −2 | 1.96% |
|  |  | Waist | 84.5 | 82 | −2.5 | 2.96% |
|  |  | Navel | 103 | 96 | −7 | 6.80% |
|  |  | Lower abdomen | 106 | 101.5 | −4.5 | 4.25% |
|  | Zone 2 | Right Arm | 32 | 30.5 | −1.5 | 4.69% |
|  |  | Left Arm | 32 | 30.5 | −1.5 | 4.69% |
|  | Zone 3 | Leg Contours | 98.5 | 94 | −4.5 | 4.57% |
|  |  | Right Leg | 63.5 | 60 | −3.5 | 5.51% |
|  |  | Left Leg | 60.5 | 57.5 | −3 | 4.96% |

-continued

| | | Example 006 | | | | |
|---|---|---|---|---|---|---|
| Patient Information | Sex | | Femenin | | | |
| Contexture and clinical data | | Thick contexture, Overweight, Height 1.64 mts, removal of thyroid. | | | | |
| | Age | | 25 years | | | |
| | Basic Pathology | | Thyroid | | | |
| | Medicines | | Eutirox 100 mg daily. | | | |
| Treatment Information | | | | | | |
| | Number of sessions 1 | | 20 minutes working time per Zone, reaching up to 60 minutes of treatment. | | | |
| Obtained Results | | | | | | |
| Body Size | Zones | | Before | After | Diference | % Decrease |
| | Zone 1 | Sleeveless | 101 | 98.5 | −2.5 | 2.48% |
| | | Breast | 107 | 103.5 | −3.5 | 3.27% |
| | | Waist | 97 | 93.5 | −3.5 | 3.61% |
| | | Navel | 113 | 105 | −8 | 7.08% |
| | | Lower abdomen | 114.5 | 109.5 | −5 | 4.37% |
| | Zone 2 | Right Arm | 36.5 | 34.5 | −2 | 5.48% |
| | | Left Arm | 37.5 | 36 | −1.5 | 4.00% |
| | Zone 3 | Leg Contours | 114 | 111 | −3 | 2.63% |
| | | Right Leg | 71 | 68 | −3 | 4.23% |
| | | Left Leg | 69 | 66.5 | −2.5 | 3.62% |

| | | Example 007 | | | | |
|---|---|---|---|---|---|---|
| Patient Information | Sex | | Masculin | | | |
| Contexture and clinical data | | Older man overwheighed, Diabetic, Height 1.78 mts. Thick Contexture. | | | | |
| | Age | | 56 years | | | |
| | Basic Pathology | | Diabetes Melitis | | | |
| | Medicines | | Trayenta Duo | | | |
| Treatment Information | | | | | | |
| | Number of sessions 1 | | Trabajamos 10 minutos por Zone, reaching up to 20 minutes of treatment. | | | |
| Obtained Results | | | | | | |
| Body Size | Zones | | Before | After | Diference | % Decrease |
| | Zone 1 | Sleeveless | 114 | 111 | −3 | 2.63% |
| | | Breast | 116 | 112.5 | −3.5 | 3.02% |
| | | Waist | 110 | 107 | −3 | 2.73% |
| | | Navel | 116 | 113.5 | −2.5 | 2.16% |
| | | Lower abdomen | 115 | 109 | −6 | 5.22% |
| | Zone 2 | Right Arm | 36 | 34.5 | −1.5 | 4.17% |
| | | Left Arm | 35.5 | 33.5 | −2 | 5.63% |

| | | Example 008 | | | | |
|---|---|---|---|---|---|---|
| Patient Information | Sex | | Femenin | | | |
| Contexture and clinical data | | Alt. 1.60 mts. Cont. Media, Grasa Abdominal y Operada de Cancer Mamario | | | | |
| | Age | | 57 years | | | |
| | Basic Pathology | | Cancer Mamario y Bochornos | | | |
| | Medicines | | Venlax | | | |
| Treatment Information | | | | | | |
| | Number of sessions 1 | | Trabajamos 20 minutos por Zone, reaching up to 40 minutes of treatment. | | | |
| Obtained Results | | | | | | |
| Body Size | Zones | | Before | After | Diference | % Decrease |
| | Zone 1 | Sleeveless | 97 | 91 | −6 | 6.19% |
| | | Breast | 96 | 94.5 | −1.5 | 1.56% |
| | | Waist | 90 | 85.5 | −4.5 | 5.00% |
| | | Navel | 92 | 87 | −5 | 5.43% |
| | | Lower abdomen | 99 | 95 | −4 | 4.04% |
| | Zone 2 | Right Arm | 30 | 29 | −1 | 3.33% |
| | | Left Arm | 30 | 29 | −1 | 3.33% |

| | | Example 009 | |
|---|---|---|---|
| Patient Information | Sex | | Femenin |
| Contexture and clinical data | | Cont. Mediana a Delgada, Alt 1.69 mts. Sufre de Colon Irritable y Depression | |
| | Age | | 43 years |
| | Basic Pathology | | Colon Irritable y Depression |
| | Medicines | | Debridat Forte y Pristiq como Antidepresivo. Dieta del Genotipo |
| Treatment Information | | | |
| | Number of sessions 1 | | Trabajamos 30 minutos por Zone, reaching up to 60 minutes of treatment. |

| Obtained Results Body Size | Zones | | Before | After | Diference | % Decrease |
|---|---|---|---|---|---|---|
| | Zone 1 | Sleeveless | 89.5 | 84 | −5.5 | 6.15% |
| | | Breast | 93.5 | 90 | −3.5 | 3.74% |
| | | Waist | 76 | 73 | −3 | 3.95% |
| | | Navel | 86 | 81 | −5 | 5.81% |
| | | Lower abdomen | 91 | 88 | −3 | 3.30% |
| | Zone 2 | Right Arm | 27 | 26 | −1 | 3.70% |
| | | Left Arm | 27 | 26 | −1 | 3.70% |

Example 010

| Patient Information Contexture and clinical data | Sex | Femenin |
|---|---|---|
| | | Medium body shape. Gymansium three times a week, Insulin resistance, Height 1.64 cm |
| | Age | 21 year old |
| | Basic Pathology | Insulin Resistance |
| | Medicine | Glafornil 1.000 mg per day |
| Treatment Information | | |
| | Number of sessions 1 | 20 minutes working time per Zone, reaching up to 60 minutes of treatment. |

| Obtained Results Body Size | Zones | | Before | After | Diference | % Decrease |
|---|---|---|---|---|---|---|
| | Zone 1 | Sleeveless | 88 | 85.5 | −3.5 | 3.98% |
| | | Breast | 92.5 | 91 | −1.5 | 1.62% |
| | | Waist | 78 | 73.5 | −5.5 | 7.05% |
| | | Navel | 87 | 82.5 | −5.5 | 6.32% |
| | | Lower abdomen | 93 | 89 | −4 | 4.30% |
| | Zone 2 | Right Arm | 29 | 27.5 | −2.5 | 8.62% |
| | | Left Arm | 28.5 | 26.5 | −2.5 | 8.77% |
| | Zone 3 | Leg Contours | 93.5 | 89 | −4.5 | 4.81% |
| | | Right Arm | 60 | 57.5 | −3.5 | 5.83% |
| | | Left Arm | 59 | 57 | −2 | 3.39% |

Example 003

| Patient Information Body shape and clinical data | Sex | Femenin |
|---|---|---|
| | | Height 1.65 mts. Overweight. Thick body shape, Sedentary |
| | Age | 30 year old |
| | Basic Pathology | Depression |
| | Medicines | Antidepressants |
| Treatment Information | | |
| | Number of sessions 7 | Working 20 minutes each zone, reaching up to 40 minutes per session |

| Obtained Results Body Size | Zones | | Before | After | Diference | % Decrease |
|---|---|---|---|---|---|---|
| | Zone 1 | Sleeveless | 92 | 88 | −4 | 4.35% |
| | | Breast | 101 | 95.5 | −5.5 | 5.45% |
| | | Waist | 83 | 79 | −4 | 4.82% |
| | | Navel | 93 | 83.5 | −9.5 | 10.22% |
| | | Lower abdomen | 95 | 89 | −6 | 6.32% |
| | Zone 2 | Right Arm | 30.5 | 27.5 | −3 | 9.84% |
| | | Left Arm | 31 | 26 | −5 | 16.13% |

Example 004

| Patient Information Body shape and clinical data | Sex | Masculin |
|---|---|---|
| | | Height 1.75 mts, Medium body shape, Overweigth, high abdominal fat content |
| | Age | 29 year old |
| | Basic Pathology | Depression |
| | Medicines | Antidepressants |
| Treatment Information | | |
| | Number of sessions 1 | Working 30 minutes per Zone, reaching up to 90 minutes of treatment. |

| Obtained Results Body Size | Zones | | Before | After | Diference | % Decrease |
|---|---|---|---|---|---|---|
| | Zone 1 | Sleeveless | 106 | 101 | −5 | 4.72% |
| | | Breast | 102 | 101 | −1 | 0.98% |
| | | Waist | 92 | 88.5 | −4.5 | 4.89% |
| | | Navel | 103 | 96.5 | −6.5 | 6.31% |
| | | Lower abdomen | 105 | 101 | −4 | 3.81% |
| | Zone 2 | Right Arm | 31 | 29.5 | −1.5 | 4.84% |
| | | Left Arm | 30 | 29 | −1 | 3.33% |
| | Zone 3 | Leg Contours | 108 | 103 | −5 | 4.63% |

-continued

|  |  |  | | | | |
|---|---|---|---|---|---|---|
|  |  | Right Leg | 69 | 66.5 | −2.5 | 3.62% |
|  |  | Left Leg | 67 | 65 | −2 | 2.99% |

Example 005

| | | | | | | |
|---|---|---|---|---|---|---|
| Patient Information Body shape and clinical data | Sex | | \multicolumn{5}{l}{Femenin} |
|  |  | | Thick body shape, Overweight, Height 1.58 mts, Healthy. | | | |
|  | Age | | 38 year old | | | |
|  | Basic Pathology | | None | | | |
|  | Medicines | | None | | | |
| Treatment Information |  | | | | | |
|  | Number of sessions 1 | | 20 minutes working time per Zone, reaching up to 60 minutes of treatment. | | | |

| | | | | | | |
|---|---|---|---|---|---|---|
| Obtained Results Body Size | Zones | | Before | After | Diference | % Decrease |
|  | Zone 1 | Sleeveless | 96 | 93 | −3 | 3.13% |
|  |  | Breast | 102 | 100 | −2 | 1.96% |
|  |  | Waist | 84.5 | 82 | −2.5 | 2.96% |
|  |  | Navel | 103 | 96 | −7 | 6.80% |
|  |  | Lower abdomen | 106 | 101.5 | −4.5 | 4.25% |
|  | Zone 2 | Right Arm | 32 | 30.5 | −1.5 | 4.69% |
|  |  | Left Arm | 32 | 30.5 | −1.5 | 4.69% |
|  | Zone 3 | Leg Contours | 98.5 | 94 | −4.5 | 4.57% |
|  |  | Right Leg | 63.5 | 60 | −3.5 | 5.51% |
|  |  | Left Leg | 60.5 | 57.5 | −3 | 4.96% |

Example 006

| | | | | | | |
|---|---|---|---|---|---|---|
| Patient Information Body shape and clinical data | Sex | | Femenin | | | |
|  |  | | Thick body shape, Overweight, Height 1.64 mts, removal of thyroid. | | | |
|  | Age | | 25 year old | | | |
|  | Basic Pathology | | Thyroid | | | |
|  | Medicines | | Eutirox 100 mg daily. | | | |
| Treatment Information |  | | | | | |
|  | Number of sessions 1 | | 20 minutes working time per Zone, reaching up to 60 minutes of treatment. | | | |

| | | | | | | |
|---|---|---|---|---|---|---|
| Obtained Results Body Size | Zones | | Before | After | Diference | % Decrease |
|  | Zone 1 | Sleeveless | 101 | 98.5 | −2.5 | 2.48% |
|  |  | Breast | 107 | 103.5 | −3.5 | 3.27% |
|  |  | Waist | 97 | 93.5 | −3.5 | 3.61% |
|  |  | Navel | 113 | 105 | −8 | 7.08% |
|  |  | Lower abdomen | 114.5 | 109.5 | −5 | 4.37% |
|  | Zone 2 | Right Arm | 36.5 | 34.5 | −2 | 5.48% |
|  |  | Left Arm | 37.5 | 36 | −1.5 | 4.00% |
|  | Zone 3 | Leg Contours | 114 | 111 | −3 | 2.63% |
|  |  | Right Leg | 71 | 68 | −3 | 4.23% |
|  |  | Left Leg | 69 | 66.5 | −2.5 | 3.62% |

Example 007

| | | | | | | |
|---|---|---|---|---|---|---|
| Patient Information Body shape and clinical data | Sex | | Masculin | | | |
|  |  | | Older man overwheighed, Diabetic, Height 1.78 mts. Thick body shape | | | |
|  | Age | | 56 year old | | | |
|  | Basic Pathology | | Diabetes Mellitus | | | |
|  | Medicines | | Trayenta Duo | | | |
| Treatment Information |  | | | | | |
|  | Number of sessions 1 | | 10 minutes working time per Zone, reaching up to 20 minutes of treatment. | | | |

| | | | | | | |
|---|---|---|---|---|---|---|
| Obtained Results Body Size | Zones | | Before | After | Diference | % Decrease |
|  | Zone 1 | Sleeveless | 114 | 111 | −3 | 2.63% |
|  |  | Breast | 116 | 112.5 | −3.5 | 3.02% |
|  |  | Waist | 110 | 107 | −3 | 2.73% |
|  |  | Navel | 116 | 113.5 | −2.5 | 2.16% |
|  |  | Lower abdomen | 115 | 109 | −6 | 5.22% |
|  | Zone 2 | Right Arm | 36 | 34.5 | −1.5 | 4.17% |
|  |  | Left Arm | 35.5 | 33.5 | −2 | 5.63% |

-continued

| Example 008 | | | | | | |
|---|---|---|---|---|---|---|
| Patient Information | Sex | Femenin | | | | |
| Body shape and clinical data | | Height 1.60 mts., Medium Conetxt, Abdominal fat and with Brest Cancer operation | | | | |
| | Age | 57 year old | | | | |
| | Basic Pathology | Breast Cancer and Hot Flashes | | | | |
| | Medicines | Venlax | | | | |
| Treatment Information | Number of sessions 1 | 20 minutes working time per Zone, reaching up to 40 minutes of treatment. | | | | |
| Obtained Results Body Size | Zones | | Before | After | Diference | % Decrease |
| | Zone 1 | Sleeveless | 97 | 91 | −6 | 6.19% |
| | | Breast | 96 | 94.5 | −1.5 | 1.56% |
| | | Waist | 90 | 85.5 | −4.5 | 5.00% |
| | | Navel | 92 | 87 | −5 | 5.43% |
| | | Lower abdomen | 99 | 95 | −4 | 4.04% |
| | Zone 2 | Right Arm | 30 | 29 | −1 | 3.33% |
| | | Left Arm | 30 | 29 | −1 | 3.33% |

| Example 009 | | | | | | |
|---|---|---|---|---|---|---|
| Patient Information | Sex | Femenin | | | | |
| Body shape and clinical data | | Medium or thin body shape, Height 1.69 mts., suffering irritable bowel and Depression | | | | |
| | Age | 43 year old | | | | |
| | Basic Pathology | Irritable Bowel and Depression | | | | |
| | Medicines | Debridat Forte and Pristiq as Antidepressant. Genotype Diet | | | | |
| Treatment Information | Number of sessions 1 | 30 minutes working time per Zone, reaching up to 60 minutes of treatment. | | | | |
| Obtained Results Body Size | Zones | | Before | After | Diference | % Decrease |
| | Zone 1 | Sleeveless | 89.5 | 84 | −5.5 | 6.15% |
| | | Breast | 93.5 | 90 | −3.5 | 3.74% |
| | | Waist | 76 | 73 | −3 | 3.95% |
| | | Navel | 86 | 81 | −5 | 5.81% |
| | | Lower abdomen | 91 | 88 | −3 | 3.30% |
| | Zone 2 | Right Arm | 27 | 26 | −1 | 3.70% |
| | | Left Arm | 27 | 26 | −1 | 3.70% |

| Example 010 | | | | | | |
|---|---|---|---|---|---|---|
| Patient Information | Sex | Femenin | | | | |
| Body shape and clinical data | | Medium body shape. Gymansium three times a week, Insulin resistance, Height 1.64 cm | | | | |
| | Age | 21 year old | | | | |
| | Basic Pathology | Insulin Resistance | | | | |
| | Medicines | Glafornil 1.000 mg per day | | | | |
| Treatment Information | Number of sessions 1 | 20 minutes working time per Zone, reaching up to 60 minutes of treatment. | | | | |
| Obtained Results Body Size | Zones | | Before | After | Diference | % Decrease |
| | Zone 1 | Sleeveless | 88 | 85.5 | −3.5 | 3.98% |
| | | Breast | 92.5 | 91 | −1.5 | 1.62% |
| | | Waist | 78 | 73.5 | −5.5 | 7.05% |
| | | Navel | 87 | 82.5 | −5.5 | 6.32% |
| | | Lower abdomen | 93 | 89 | −4 | 4.30% |
| | Zone 2 | Right Arm | 29 | 27.5 | −2.5 | 8.62% |
| | | Left Arm | 28.5 | 26.5 | −2.5 | 8.77% |
| | Zone 3 | Leg Contours | 93.5 | 89 | −4.5 | 4.81% |
| | | Right Leg | 60 | 57.5 | −3.5 | 5.83% |
| | | Left Leg | 59 | 57 | −2 | 3.39% |

| Example 011 | | |
|---|---|---|
| Patient Information | Sex | Femenin |
| Body shape and clinical data | | Medium body shape, Height 1.62 mts, Engorged Abdomen, Colon removal. |
| | Age | 48 year old |
| | Basic Pathology | Diverticulitis (Colon Removal) |
| | Medicines | None, Spetial Diet. |
| Treatment Information | Number of sessions 1 | 20 minutes working time per Zone, reaching up to 60 minutes of treatment. |

-continued

| Obtained Results Body Size | Zones | | Before | After | Diference | % Decrease |
|---|---|---|---|---|---|---|
| | Zone 1 | Sleeveless | 96.5 | 92.5 | −4 | 4.15% |
| | | Breast | 105 | 101.5 | −3.5 | 3.33% |
| | | Waist | 84.5 | 81 | −3.5 | 4.14% |
| | | Navel | 94.5 | 89 | −5.5 | 5.82% |
| | | Lower abdomen | 100.5 | 97 | −3.5 | 3.48% |
| | Zone 2 | Right Arm | 32 | 30.5 | −1.5 | 4.69% |
| | | Left Arm | 31.5 | 30 | −1.5 | 4.76% |
| | Zone 3 | Leg Contours | 91 | 89 | −2 | 2.20% |
| | | Right Leg | 61.5 | 59.5 | −2 | 3.25% |
| | | Left Leg | 60.5 | 58.5 | −2 | 3.31% |

Example 012

| Patient Information Body shape and clinical data | Sex | Femenin |
|---|---|---|
| | | Medium body shape/skinny, Height 1.59 mts, 2 times a wekk sport, healthy diet |
| | Age | 32 year old |
| | Basic Pathology | Irritable Bowel and Depression |
| | Medicines | Contraceptives, Lerogin for Colon, Stressam 50 mg. Sertraline Zoloft |
| Treatment Information | Number of sessions 1 | 15 minutes working time per each zone, with up to 30 minutes per session |

| Obtained Results Body Size | Zones | | Before | After | Diference | % Decrease |
|---|---|---|---|---|---|---|
| | Zone 1 | Waist | 77 | 72.5 | −4.5 | 5.84% |
| | | Navel | 89.5 | 82.5 | −7 | 7.82% |
| | | Lower abdomen | 96.5 | 88.5 | −10 | 10.36% |
| | Zone 2 | Leg Contours | 98.5 | 86 | −12.5 | 12.69% |
| | | Right Leg | 60.5 | 57 | −3.5 | 5.79% |
| | | Left Leg | 59.5 | 56 | −3.5 | 5.88% |

Example 013

| Patient Information Body shape and clinical data | Sex | Masculin |
|---|---|---|
| | | Fatter body shape/Overwieght, Height. 1.70 mts, healthy. Sedentary, Older man. |
| | Age | 63 year old |
| | Basic Pathology | None |
| | Medicines | None |
| Treatment Information | Number of sessions 1 | 40 minutes working time per Zone, masculine thicker skyn. |

| Obtained Results Body Size | Zones | | Before | After | Diference | % Decrease |
|---|---|---|---|---|---|---|
| | Zone 1 | Sleeveless | 111 | 108 | −3 | 2.70% |
| | | Breast | 114 | 112 | −2 | 1.75% |
| | | Waist | 106.5 | 104.5 | −3 | 2.82% |
| | | Navel | 117 | 111.5 | −6.5 | 5.56% |
| | | Lower abdomen | 119 | 114 | −5 | 4.20% |

Example 014

| Patient Information Body shape and clinical data | Sex | Femenin |
|---|---|---|
| | | Fatter body shape/Overwieght, Height 1.64 mts, cardiovasc. risk, antiphosph. syndrome |
| | Age | 38 year old |
| | Basic Pathology | Antiphospholipid Syndrome |
| | Medicines | Anticoagulant |
| Treatment Information | Number of sessions 1 | 20 minutes working time per Zone, reaching up to 60 minutes of treatment. |

| Obtained Results Body Size | Zones | | Before | After | Diference | % Decrease |
|---|---|---|---|---|---|---|
| | Zone 1 | Sleeveless | 106.5 | 101.5 | −5 | 4.69% |
| | | Breast | 114 | 111 | −3 | 2.63% |
| | | Waist | 104.5 | 101 | −3.5 | 3.35% |
| | | Navel | 116 | 111 | −5 | 4.31% |
| | | Lower abdomen | 122 | 115.5 | −6.5 | 5.33% |
| | Zone 2 | Right Arm | 39 | 37 | −2 | 5.13% |
| | | Left Arm | 38.5 | 36.5 | −2 | 5.19% |
| | Zone 3 | Leg Contours | 106 | 102 | −4 | 3.77% |
| | | Right Leg | 69 | 66 | −3 | 4.35% |
| | | Left Leg | 71 | 67.5 | −3.5 | 4.93% |

-continued

| Example 015 | | | | | | |
|---|---|---|---|---|---|---|
| Patient Information Body shape and clinical data | Sex | Femenin | | | | |
| | Age | Medium body shape/Thinny, Height 1.58 mts Dance practice 3 time per week, healthy diet | | | | |
| | | 25 year old | | | | |
| | Basic Pathology | Adeniod cist | | | | |
| | Medicines | Fluranizine, Comprit, Dolipran. | | | | |
| Treatment Information | Number of sessions 1 | 15 minutes time per Zone, reaching up to 30 minutes of treatment. | | | | |
| Obtained Results Body Size | Zones | | Before | After | Diference | % Decrease |
| | Zone 1 | Sleeveless | 97.5 | 94 | −3.5 | 3.59% |
| | | Breast | 96 | 93 | −3 | 3.13% |
| | | Waist | 85 | 82.5 | −2.5 | 2.94% |
| | | Navel | 96 | 88 | −8 | 8.33% |
| | | Lower abdomen | 99 | 98 | −1 | 1.01% |
| | Zone 2 | Right Arm | 29 | 28 | −1 | 3.45% |
| | | Left Arm | 30 | 28.5 | −1.5 | 5.00% |

| Example 016 | | | | | | |
|---|---|---|---|---|---|---|
| Patient Information Body shape and clinical data | Sex | Femenin | | | | |
| | Age | Thynny shape, height 1.64 cms. Engorged Abdomen, Insuline Resistance, Hyperthyroidism | | | | |
| | | 49 year old | | | | |
| | Basic Pathology | Insuline Resistance, Hyperthyroidism | | | | |
| | Medicines | Eutirox and Glafornil 1000 mg per day | | | | |
| Treatment Information | Number of sessions 1 | 20 minutes working time per Zone, reaching up to 60 minutes detratamieno. | | | | |
| Obtained Results Body Size | Zones | | Before | After | Diference | % Decrease |
| | Zone 1 | Sleeveless | 93 | 91 | −2 | 2.15% |
| | | Breast | 92 | 89 | −3 | 3.26% |
| | | Waist | 87.5 | 83 | −4.5 | 5.14% |
| | | Navel | 95 | 91.5 | −3.5 | 3.68% |
| | | Lower abdomen | 102 | 95 | −7 | 6.86% |
| | Zone 2 | Right Arm | 31 | 29.5 | −1.5 | 4.84% |
| | | Left Arm | 30.5 | 30 | −1.5 | 4.92% |
| | Zone 3 | Leg Contours | 88.5 | 86 | −1.5 | 1.69% |
| | | Right Leg | 59.5 | 57.5 | −2 | 3.36% |
| | | Left Leg | 60.5 | 56 | −4.5 | 7.44% |

| Example 017 | | | | | | |
|---|---|---|---|---|---|---|
| Patient Information Body shape and clinical data | Sex | Femenin | | | | |
| | Age | Medium body shape, Engorged Abdomen, Sedentay, Latex Alergy. | | | | |
| | | 39 year old | | | | |
| | Basic Pathology | Latex Alergy | | | | |
| | Medicines | None | | | | |
| Treatment Information | Number of sessions 1 | 15 minutes working time per Zone, reaching up to 45 minutes of treatment. | | | | |
| Obtained Results Body Size | Zones | | Before | After | Diference | % Decrease |
| | Zone 1 | Sleeveless | 100 | 98 | −2 | 2.00% |
| | | Breast | 101.5 | 99.5 | −2 | 1.97% |
| | | Waist | 88 | 86 | −2 | 2.27% |
| | | Navel | 97 | 91 | −6 | 6.19% |
| | | Lower abdomen | 104 | 97 | −7 | 6.73% |
| | Zone 2 | Right Arm | 31 | 30 | −1 | 3.23% |
| | | Left Arm | 30.5 | 29.5 | −1 | 3.28% |
| | Zone 3 | Leg Contours | 93 | 88.5 | −4.5 | 4.84% |
| | | Right Leg | 60 | 57.5 | −2.5 | 4.17% |
| | | Left Leg | 59 | 56 | −3 | 5.08% |

| Example 018 | |
|---|---|
| Patient Information Body shape and clinical data | Sex: Femenin |
| | Old woman with a concordant body shape and with many Basis pathology. |
| | Age: 61 year old |
| | Basic Pathology: Insuline resistance, Artereal Hypertension, Lupusprobable, Arthritit, Rosacea. |
| | Medicines: Plaquinel, Forget, Glafornil and Ravotril. |
| Treatment Information | Number of sessions 1: 15 minutes working time per Zone, reaching up to 30 minutes of treatment. |

| Obtained Results Body Size | Zones | | Before | After | Diference | % Decrease |
|---|---|---|---|---|---|---|
| | Zone 1 | Sleeveless | 98 | 95 | −3 | 3.06% |
| | | Breast | 100 | 100 | 0 | 0.00% |
| | | Waist | 94 | 88 | −6 | 6.38% |
| | | Navel | 95 | 93 | −2 | 2.11% |
| | | Lower abdomen | 95.5 | 93.5 | −2 | 2.09% |
| | Zone 2 | Right Arm | 31 | 30 | −1 | 3.23% |
| | | Left Arm | 31.5 | 31 | −0.5 | 1.59% |

Example 019

| Patient Information | Sex | Masculin |
|---|---|---|
| Body shape and clinical data | | Medium body shape, Sport man, healthy diet, Height 1.78 mts. |
| | Age | 50 year old |
| | Basic Pathology | None |
| | Medicines | None |
| Treatment Information | | |
| | Number of sessions 1 | 40 minutes working time per zone, maculine thicker skin |

| Obtained Results Body Size | Zones | | Before | After | Diference | % Decrease |
|---|---|---|---|---|---|---|
| | Zone 1 | Sleeveless | 101.5 | 95 | −5.5 | 5.42% |
| | | Breast | 91 | 87.5 | −4.5 | 4.95% |
| | | Waist | 86.5 | 85 | −1.5 | 1.73% |
| | | Navel | 86 | 83 | −3 | 3.49% |

Example 020

| Patient Information | Sex | Femenin |
|---|---|---|
| Body shape and clinical data | | Medium body shape, No Cardiovascular risk, No diet and non sporte practice |
| | Age | 44 year old |
| | Basic Pathology | Hypotiroidism and Menier Sindrome |
| | Medicines | Eutirox and Microser. |
| Treatment Information | | |
| | Number of sessions 1 | 20 minutes working time each zone, reaching up to 60 minutes of treatment. |

| Obtained Results Body Size | Zones | | Before | After | Diference | % Decrease |
|---|---|---|---|---|---|---|
| | Zone 1 | Sleeveless | 91.5 | 89 | −2.5 | 2.73% |
| | | Breast | 95 | 92.5 | −2.5 | 2.63% |
| | | Waist | 84 | 81.5 | −2.5 | 2.98% |
| | | Navel | 95.5 | 89.5 | −6 | 6.28% |
| | | Lower abdomen | 97 | 94.5 | −2.5 | 2.58% |
| | Zone 2 | Right Arm | 29 | 28 | −1 | 3.45% |
| | | Left Arm | 29 | 28 | −1 | 3.45% |
| | Zone 3 | Leg Contours | 99 | 94.5 | −4.5 | 4.55% |
| | | Right Leg | 62 | 60 | −2 | 3.23% |
| | | Left Leg | 60 | 58.5 | −1.5 | 2.50% |

This data reveals that the best results are achieved when the treatment is carried out with the subject standing, and that a substantial reduction in the perimeter of the areas studied is always obtained. The reduction achieved was between 1 and 3.5 cm; more preferably between 3.5 and 5.5 cm and even more preferably between 5.5 and 11 cm. On average, it is possible to define that 10% to 15% of reduction are surprisingly reached in some zones and in other areas over 5%. This percentage being understood as the difference in cms observed divided by the measurement before the treatment applying the pharmaceutical composition and Multiplied by 100.

All documents referred to in this application are fully incorporated in this document. This invention is susceptible to considerable variation in its practice. It is therefore not intended that the foregoing description limit the invention to the examples presented herein, nor should this application be construed as limiting the description thereof.

The invention claimed is:

1. A topical, reductive cosmetic composition, comprising up to 15% by weight of hydrolyzed keratin and micrometer-sized Sulphur, and a remainder of the composition comprising water, compatibilizers, surfactants, thickeners, preservatives and/or flavoring agents.

2. The cosmetic composition of claim 1, wherein the amount of hydrolyzed keratin is between 1 and 10% by weight of the composition.

3. The cosmetic composition of claim 1, wherein the amount of Sulphur is between 0.1 and 4% by weight of the composition.

4. The cosmetic composition of claim 1, wherein the surfactants comprise a first surfactant and a second surfactant, and wherein the first surfactant is triethanolamine dodecyl sulfate.

5. The cosmetic composition of claim 4, wherein the triethanolamine dodecyl sulfate is present between 10 and 45% by weight of the composition.

6. The cosmetic composition of claim 4, wherein the second surfactant is cocamidopropyl betaine.

7. The cosmetic composition of claim 6, wherein the cocamidopropyl betaine is present between 10 and 45% by weight of the composition.

8. The cosmetic composition of claim 1 further comprising a cleaning agent, wherein the cleaning agent is disodium cocoamphodiacetate.

9. The cosmetic composition of claim 8, wherein the disodium cocoamphodiacetate is present in a range from 1 to 5% by weight of the composition.

10. The cosmetic composition of claim 9, wherein the amount of disodium cocoamphodiacetate is about 2% by weight of the composition.

11. The cosmetic composition of claim 1, wherein the thickener is methyl glucose dioleate (PEG-120).

12. The cosmetic composition of claim 11, wherein the methyl glucose dioleate (PEG-120) is present in a range from 1 to 10% by weight of the composition.

13. The cosmetic composition of claim 11, wherein the amount of methyl glucose dioleate (PEG-120) is about 6% by weight of the composition.

14. The cosmetic composition of claim 1, wherein the preservative is DMDM hydantoin.

15. The cosmetic composition of claim 14, wherein the DMDM hydantoin is present in a range from 1 to 10% by weight of the composition.

16. The cosmetic composition of claim 15, wherein the amount of DMDM hydantoin is about 2% by weight of the composition.

17. The cosmetic composition of claim 1, wherein the preservative is iodopropynyl butylcarbamate.

18. The cosmetic composition of claim 17, wherein the iodopropynyl butylcarbamate is present in a range from 0.5 to 4% by weight of the composition.

19. The cosmetic composition of claim 18, wherein the amount of iodopropynyl butylcarbamate is about 1% by weight of the composition.

20. The cosmetic composition of claim 1, wherein the compatibilizer is castor oil.

21. The cosmetic composition of claim 20, wherein the castor oil is present in a range from 0.5 to 10% by weight of the composition.

22. The cosmetic composition of claim 21, wherein the amount of castor oil is about 4.9% by weight of the composition.

23. The cosmetic composition of claim 1, wherein the flavoring agent is present in the amount of 0.1% by weight of the composition.

24. The cosmetic composition of claim 1, wherein the water is at least one of pure water, deionized water, mineral water and thermal water.

25. The cosmetic composition of claim 24, wherein the water is pure water.

26. The cosmetic composition of claim 24, wherein the water is deionized water.

27. The cosmetic composition of claim 24, wherein the water is mineral water.

28. The cosmetic composition of claim 24, wherein the water is thermal water.

29. The cosmetic composition of claim 24, wherein an aqueous phase of the composition comprises between 20 to 70% by weight of the composition, preferably between 20 to 50% by weight of the composition, and more preferably between 30 to 50% by weight of the composition.

30. The cosmetic composition of claim 24, wherein the composition is in a form selected from at least one of an oil-in-water emulsion, a water-in-oil emulsion, a lotion, a gel and a soap.

31. The cosmetic composition of claim 24, wherein the composition is a body thinning composition.

32. Use of the cosmetic composition of claim 1 to reduce adipose tissue.

33. A cosmetic method for care and/or treatment of a body, wherein the cosmetic composition of claim 1 is applied over adipose regions of the body for the duration of between 5 and 20 minutes.

34. The method according to claim 33, wherein the method includes a treatment to reduce cellulite, and/or for weight loss.

35. The method according to claim 33, wherein the adipose regions of the body include at least one of waist, hips, thighs, legs, arms, submental area, and submandibular under sternocleidomastoid muscle.

36. The method according to claim 1, wherein the composition is applied to the body while a patient is in a standing position.

* * * * *